US008708559B2

(12) United States Patent
Piscsalko et al.

(10) Patent No.: US 8,708,559 B2
(45) Date of Patent: *Apr. 29, 2014

(54) PILE SENSING DEVICE AND METHOD OF USING THE SAME

(71) Applicant: Pile Dynamics, Inc., Solon, OH (US)

(72) Inventors: George R. Piscsalko, Rock Creek, OH (US); Frank Rausche, Chagrin Falls, OH (US); Dean A. Cotton, Fairview Park, OH (US); Michael Ference, Solon, OH (US)

(73) Assignee: Pile Dynamics, Inc., Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/742,888

(22) Filed: Jan. 16, 2013

(65) Prior Publication Data

US 2013/0128920 A1     May 23, 2013

Related U.S. Application Data

(63) Continuation of application No. 13/025,875, filed on Feb. 11, 2011, now Pat. No. 8,382,369.

(60) Provisional application No. 61/305,303, filed on Feb. 17, 2010.

(51) Int. Cl.
*G01K 13/00* (2006.01)
(52) U.S. Cl.
USPC ............................. 374/141; 374/137; 73/803
(58) Field of Classification Search
USPC .................................................. 374/141, 137
See application file for complete search history.

(56) References Cited

U.S. PATENT DOCUMENTS

| 3,533,502 | A | 10/1970 | Hansen |
| 5,344,335 | A | 9/1994 | Scholz et al. |
| 5,978,749 | A | 11/1999 | Likins, Jr. et al. |
| 6,301,551 | B1 * | 10/2001 | Piscalko et al. ............... 702/188 |
| 6,533,502 | B2 | 3/2003 | McVay et al. |
| 6,690,182 | B2 * | 2/2004 | Kelly et al. .................. 324/700 |
| 6,783,273 | B1 * | 8/2004 | Mullins et al. ................. 374/45 |
| 6,913,384 | B2 * | 7/2005 | Park et al. ..................... 374/102 |
| 6,988,026 | B2 | 1/2006 | Breed et al. |

(Continued)

OTHER PUBLICATIONS

International Search Report/Written Opinion dated May 6, 2011 in corresponding International Application No. PCT/US2011/024569, filed Feb. 11, 2011.

*Primary Examiner* — Lisa Caputo
*Assistant Examiner* — Nasir U Ahmed
(74) *Attorney, Agent, or Firm* — Rankin, Hill & Clark LLP

(57) ABSTRACT

A system for monitoring the forming of a solid object having a sensor string positionable in a forming structure before the curing process and a communication line extending along a string axis between a first and second end. The string further including a plurality of sensors joined to the communication line between the ends and each sensor being mounted at a set position on the line. Each sensor having a sensor body and a sensor housing and the sensor body including an electrical connecter to electrically join an electrical structure to the communication line at the set position. The electrical structure including a temperature sensor configured to monitor temperature near the set position and further including an electronic identification code corresponding to the set position of the sensor along the axis. The system further including a transmitting device for selectively communicating the temperature and identification code.

15 Claims, 7 Drawing Sheets

(56) References Cited

U.S. PATENT DOCUMENTS

| | | |
|---|---|---|
| 7,037,041 B1 | 5/2006 | Pfaff |
| 7,174,277 B2 | 2/2007 | Vock et al. |
| 7,441,464 B2 | 10/2008 | Turnbull et al. |
| 7,637,166 B2 * | 12/2009 | Hecht et al. .............. 73/803 |
| 8,061,037 B2 * | 11/2011 | Hecht .................. 29/897.34 |
| 2003/0205083 A1 | 11/2003 | Tubel et al. |

\* cited by examiner

PILE SENSING DEVICE AND METHOD OF USING THE SAME

This application is a continuation application of Non-Provisional patent application Ser. No. 13/025,875 that was filed on Feb. 11, 2011 and which claims priority in Provisional Patent Application Ser. No. 61/305,303, both of which are incorporated by reference into the specification of this application.

The invention of this application relates to a pile sensing device. More particularly, the invention of this application relates to a disposable sensing system that can be cast directly into or mounted thereon a pile or other structural object.

INCORPORATION BY REFERENCE

McVay et al. —U.S. Pat. No. 6,533,502 discloses a wireless apparatus and method for analysis of piles which is incorporated by reference herein for showing the same. In addition, Mullins et al. —U.S. Pat. No. 6,783,273 discloses a method for testing integrity of concrete shafts which is also incorporated by reference in this application for showing the same. Piscsalko et al. —U.S. Pat. No. 6,301,551 discloses a remote pile driving analyzer and is incorporated by reference in this application for showing the same. Likins Jr. et al. —U.S. Pat. No. 5,978,749 discloses a pile installation recording system and is incorporated by reference in this application for showing the same.

BACKGROUND OF THE INVENTION

Applicant has found that the invention of this application works particularly well with the installation and monitoring of piles wherein this reference is being used throughout this application. However, this application is not to be limited to piles wherein reference to piles in this application is not to limit the scope of this application.

Sensing apparatuses have been used in the building industry for a number of years. These sensing apparatuses include a wide range of devices used for a wide range of reasons in the field. This includes sensing devices that are used in connection with the installation and use of supporting structures such as piles that are used to support the weight of superstructures such as supporting the weight of buildings and bridges. As can be appreciated, it is important to both ensure that a supporting structure, such as a pile, has been properly installed and that it is in proper condition throughout its use in the field.

With respect to the installation of piles, it is important that these structures be properly constructed so that the pile can support the weight of a building or superstructure. Thus, over the years, systems have been designed to work in connection with the installation of a pile to ensure that this pile meets the building requirements for the structure. This includes sensing devices that work in connection with the driving of a pile as is shown in Piscsalko et al., U.S. Pat. No. 6,301,551. Again, the Piscsalko patent is incorporated by reference herein as background material relating to the sensing and driving of structural piles. These devices help the workers driving these piles to determine that the pile has been properly driven within the soil without over stressing the pile during the driving process.

Similarly, devices are known which are used to monitor the pile after it is driven. This includes the Piscsalko patent which includes devices that can be used to monitor the pile even after the driving process. Further, Mcvay, et al., U.S. Pat. No. 6,533,502 also discloses a device used to monitor a pile after the driving process is completed. The information produced by the systems can be used to determine the current state of the pile and for determining damage that may or may not have incurred in response to any one of a number of events including natural disasters.

However, these devices do not fully work in connection with a drilled and poured pile wherein the pouring of the pile and the quality of this pouring can determine the structural integrity of the pile once the poured material has cured. Mullins, et al., U.S. Pat. No. 6,783,273 attempts to overcome the shortcomings in the prior art by disclosing a method for testing the integrity of concrete shafts or piles. However, the device disclosed in Mullins has been found to be ineffective and to be costly to operate wherein there are still shortcomings in the art for the monitoring of the curing process of a poured pile and to ensure that the poured pile is free of inclusions.

SUMMARY OF THE INVENTION

The invention of this application relates to pile sensors and, more particularly, to a sensing system that can be embedded into a pile and which can sense different physical characteristics of the pile either during the formation of the pile or subsequent to the formation of the pile.

More particularly, one aspect of the present invention is a system to monitor the pouring and/or curing of a poured pile by including sensors positioned within the cavity that is to be poured.

More particularly, in one embodiment, the sensors can be a plurality of sensors strung to a wired system wherein the wire system extends through the cavity to be poured. However, it should be noted that the use of the term "wire" throughout this application is not to be limited to a metal based stranded wire. The wired system can be any communication link and/or conductor known in the art and that will be known in the art in the future including, but not limited to, a single pliable metallic strand or rod, multiple pliable metallic strands or rods, fiber optics, and/or wireless systems.

According to another aspect of the invention of this application, this wire system can include temperature sensors joined to the wire wherein the pile is poured around the wire sensors and the temperature sensors on the wire can monitor the temperature of the poured pile. This poured material can include, but is not limited to cement, concrete, grout and/or other pourable materials and the temperature sensors can be utilized to monitor the changing temperatures of this poured material during the curing or solidification process.

According to yet another aspect of the invention of this application, this temperature sensing data can be fed into a computer system to obtain a schematic or matrix interpretation of the curing process to determine the integrity of the pile.

According to yet other aspects of the present invention, the string sensor arrangement can include other sensing devices beyond the temperature sensors which can be utilized to monitor other physical characteristics of the pile either during or after the pouring process.

According to yet a further aspect of the invention, provided is a system for monitoring a formed solid object which is produced by introducing a material into a forming structure and solidifying the material in the forming structure into the formed solid object by a curing process, the formed solid object having a first extent and an opposite second extent, A system for monitoring a formed solid object which is produced by introducing a material into a forming structure and solidifying the material in the forming structure into the formed solid object by a curing process wherein the formed solid object has a first extent and an opposite second extent. The system having a sensor string positionable in the forming structure before the curing process and having a communication line extending along a string axis between a first end and a second end of the line. The string further including a plurality of sensors joined to the communication line between the first end and the second end and each sensor being mounted at a set position on the line. Each sensor having a sensor body and a sensor housing and the sensor body including an electrical connecter to electrically join an electrical structure to the communication line at the set position. The electrical structure including a temperature sensor configured to monitor the real time temperature of the material near the set position and further including an electronic identification code corresponding to the set position of the sensor along the axis. The sensor further including a transmitting device for selectively communicating the real time temperature and the identification code to the communication line.

According to another aspect of the invention, provided is a sensor string for the system for monitoring the formed solid object. The sensor string being positionable in a forming structure before the curing process of the non-solid material and having a communication line formed by an electric conductor having at least one wire surrounded by a wire jacket extending along a string axis between a first end and a second end. The first end having at least one lead for forming an electrical connection. The string further including a plurality of sensors joined to the communication line between the first end and the second end and each sensor being mounted to the electrical conductor at a set position along the communication line. The sensors further including a sensor body and a sensor housing and the sensor body having an electrical connecter to electrically join an electrical structure to the electrical conductor at the set position. The electrical structure including a temperature sensor configured to monitor the real time temperature of the material near the set position, the electrical structure further including an electronic identification code corresponding to the set position of the sensor along the axis and a transmitting device for selectively communicating the real time temperature and the identification code to the communication line.

According to yet a further aspect of the invention, provided is a method of measuring at least one condition of the poured structure including the steps of:

Providing a forming structure having a first extent and an opposite second extent wherein the forming structure extends along a structure axis between the first and second extents;

Providing a system for monitoring comprising at least one sensor string having a communication line extending along a string axis between a first end and a second end and a plurality of sensors joined to the communication line between the first end and the second end. Each sensor of the plurality of sensors being mounted at a set position along the communication line between the first end and the second end and including a sensor body and a sensor housing. The sensor body including an electrical connecter to electrically join an electrical structure to the communication line at the set position along the string axis and the electrical structure including a temperature sensor configured to monitor the real time temperature near the set position. The electrical structure further including an identification code corresponding to the set position of the sensor along the axis and a transmitting device for selectively communicating the real time temperature and the identification code to the communication line;

Positioning the at least one string in the forming structure wherein the first end is near the first extent and at least a portion of the string axis extends toward the second extent;

Pouring the curable material into the forming structure whereby the string is at least partially encapsulated by the curable material;

Monitoring the temperature of the plurality of sensors after the pouring step at least at specific intervals;

Associating the real time temperature of the plurality of sensors with the each sensor and with the position of the each sensor;

Combining the associated temperature and position of the plurality of sensors; and/or, Determining the at least one condition of the poured structure.

These and other objects and advantages will become apparent from the following description taken together with the accompanying drawings.

DESCRIPTION OF PREFERRED EMBODIMENTS

Figure 1:
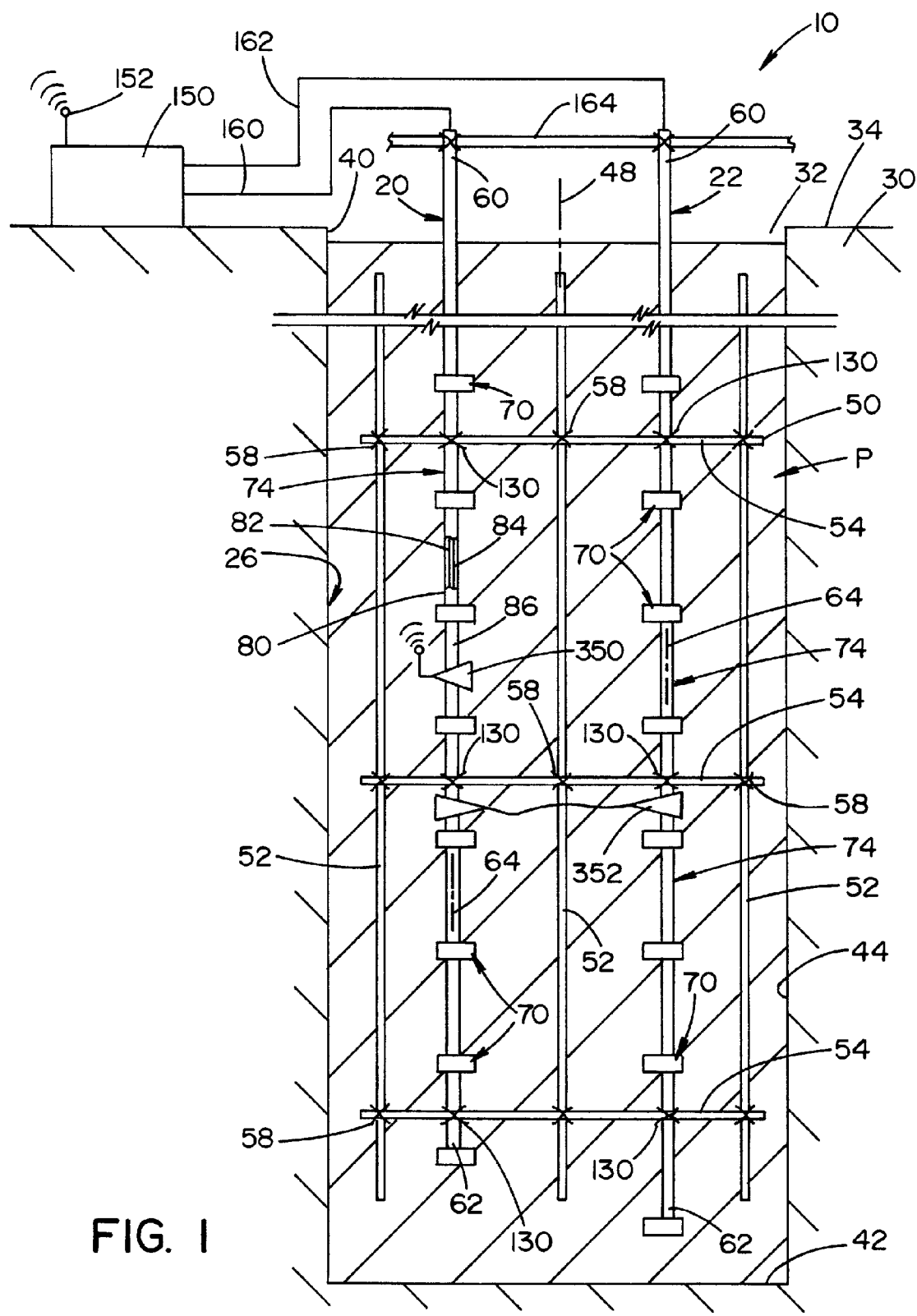
FIG. 1 is a sectional view of a drilled pile which includes the sensing device of this application.
Figure 4:
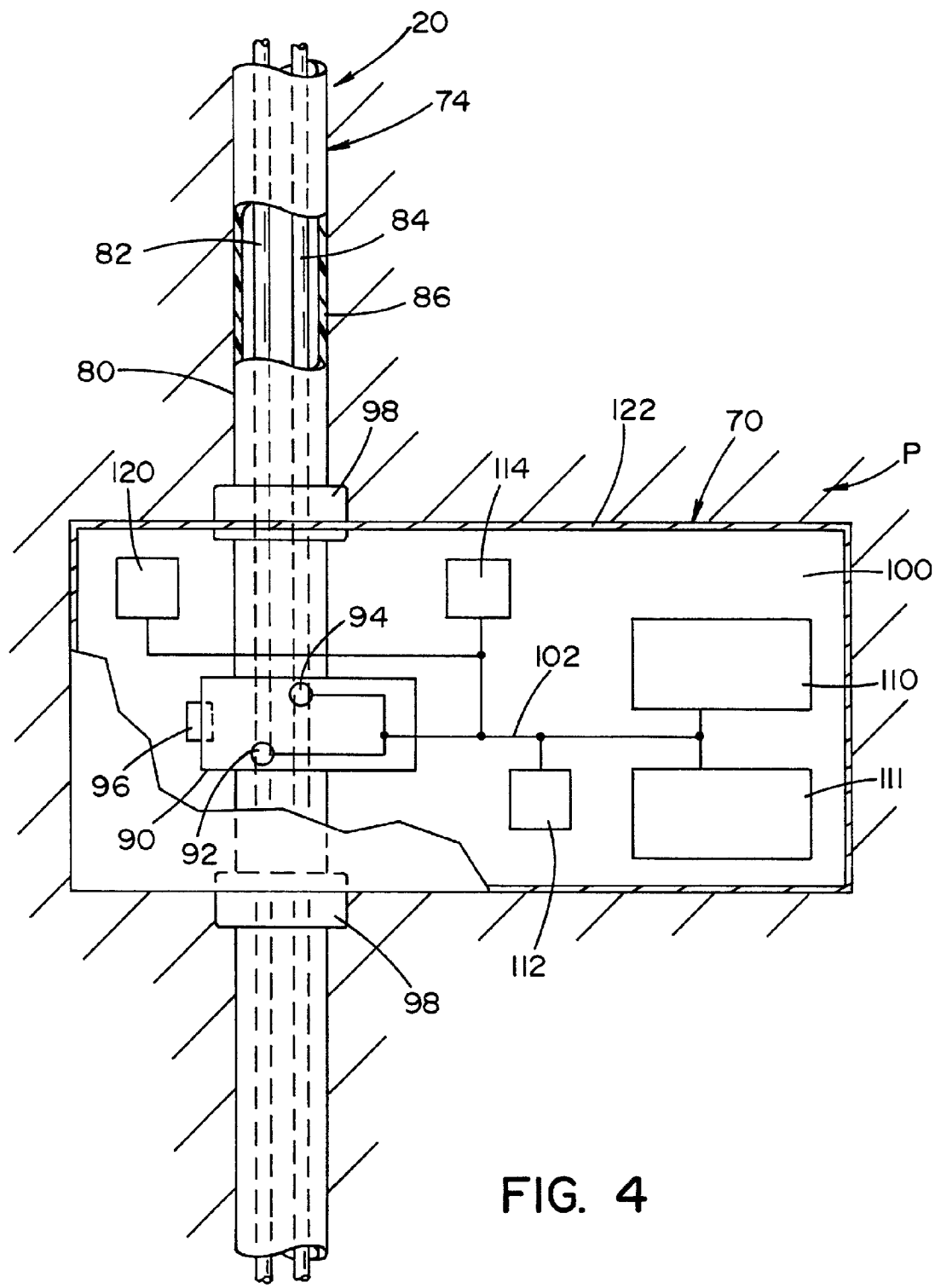
FIG. 4 is an enlarged, partially sectioned view of a sensor taken from FIG. 1.

Referring now to the drawings wherein the showings are for the purpose of illustrating preferred and alternative embodiments of the invention only and not for the purpose of limiting the same, FIGS. 1 and 4 show a system 10 which is utilized to measure a one or more characteristics of a pile P during and/or after the pouring process. More particularly, shown in this embodiment is the system with a first sensor string 20 and a second sensor string 22 for measuring the temperature changes and/or other factors in the pile during and/or after the pile has been poured. As will be discussed in greater detail below, any number of sensors strings can be used in system 10 and these can be used for both the curing process and/or after the curing process.

In this respect, and as is known in the art, a pile can be made by many different techniques. One of these techniques is to pour concrete and/or grout into a pile cavity 26 which will be generally referred to as the forming structure in that this application can be used for structures well beyond drilled and poured pile structures. However, this poured material can be any poured material to form the support structure without detracting from the invention of this application. This cavity can be produced by any means known in the art including, but not limited to, a drill process to form this hole in a ground layer 30. This cavity has an opening 32 in a surface 34 of the ground layer. This opening can represent an upper or first extent 40 of cavity 26. Cavity, in this arrangement, extends downwardly to a second or bottom extent 42 and includes side wall(s) 44 extending between the upper and lower extents along a cavity axis 48. Further, this system can be used in connection with any technique including, but not limited to Auger Cast In Place (A.C.I.P.), Drilled Shaft poured dry or under slurry (D.S.), Drilled Displacement pile (D.D.) and/or Continuous Flight Auger (C.F.A.).

Pile cavity 26 can further include a reinforcing structures including, but not limited to, a rebar cage 50 having vertical sections 52 and horizontal sections 54 joined to one another by ties or connectors 58. This structural framework can be positioned throughout the pile cavity and take any form without detracting from the invention of this application. The strings can be joined or supported by the rebar cage or can be supported by a separate structure configured only to support the string and which is separate from any reinforcing cage structure in the support structure.

Again, the sensor strings can be any number of sensor strings and can extend longitudinally down into the pile cavity parallel to cavity axis 48 or in other embodiments in other orientations such as horizontal orientations for road or bridge structures which will be discussed in greater detail below. Shown is a two string arrangement including strings 20 and 22. Each of these strings extends longitudinally into the pile cavity and can be secured to the rebar to maintain a desired position of these strings before the concrete is poured into the cavity.

Each of these strings extends between a first end 60 and a second end 62 along a string axis 64 which can be parallel to cavity axis 48. In one embodiment, first end 60 can be a transmission end and second end 62 can be a base end near or at the bottom of the cavity. However, the second or base end or ends do not need to be in alignment and these strings do not need to be parallel even though this may be preferred to maximize the accuracy of the system which will be discussed in greater detail below.

Between the ends is a plurality of sensors 70 that are each positioned at a set position along axis 64 wherein these set points are spaced designated intervals along the string line. This spacing can be any desired spacing. In one embodiment, this spacing can be uniform. In another embodiment, the spacing can be approximately six inches. In other embodiments, these sensors can be spaced approximately twelve inches from one another. In yet other embodiments, these sensors can be differently spaced for each string. Again, there are a wide range of spacings that could be used for the invention of this application. Sensor 70 are each joined to one another and supported by a support and/or communication line 74 which can substantially form strings 20, 22 wherein the sensors can be fully supported by line 74 which will also be discussed in greater detail below.

Line 74 can be formed by any method known in the art to support and/or communicate data. As can be appreciated, a support line can take many forms. Similarly, line 74 utilized as a communication line can take many forms and can be any data capable line known in the art including, but not limited to, a single pliable metallic strand or rod, multiple pliable metallic strands or rods and/or fiber optics that are covered and/or coated as is needed. Further, regardless of whether line 74 is a support or communication line, a wireless network could be utilized to transmit data in full or in part wherein in one set of embodiments, line 74 could even be a power feed for the systems of this application. In the interest of brevity, these will be generally referred to as wires. In one embodiment, line 74 is an electric conductor 80 having two wires 82 and 84 grouped together in a jacket 86. Any electrical conductor, cable or wire can be used for conductor 80 without detracting from the invention of this application. In one embodiment, wires 82 and 84 can be standard 18 gauge wire. In other embodiments, one wire can be used and in others more than two wires can be used. However, sensors 70 are joined to conductor 80 such that the sensor stay fixed relative to the conductor at a set location along the string axis. In one embodiment, sensors 70 include an electrical connector 90 that is a clip style connector; however, any electrical connector could be used without detracting from the invention of this application. This clip can be a simple locking clip that has a first barb 92 and a second barb 94 wherein barb 92 is configured to pierce jacket 86 of wire 82 to form an electrical connection with wire 82. Similarly barb 94 can be configured to pierce jacket 86 of wire 84 to form an electrical connection with wire 84. Connector 90 can further include a locking arrangement 96 that can maintain a desired locking fit between the barbs and the respective wire to maintain the electrical connection therebetween. In this embodiment, the wire can function as the "string" and fully support the sensors of system within the wire cavity at their respective set point. As can be appreciated, this system can be inexpensive to produce and can allow for a significant amount of temperature sensors to be positioned within the pile cavity. Further, in that multiple sensors can be used, these sensors can be accurately fixed at set positions wherein temperature reading for each sensor can be accurately associated with a particular location within the pile and to help produce a three dimensional temperature matrix which will be discussed in greater detail below.

In yet another embodiment, one or more sensors 70 can include a strain relief 98 to lessen the stress put on the connection between the sensor and the line. As can be appreciated, the pouring process can stress this connection wherein strain relief can redirect this stress away from the electrical connection.

In even yet other embodiments of this application, the sensors can be joined or molded into the communication line wherein both the line and the sensor are jacketed by the same cable jacket (or secondary layer) thereby further protecting the sensor, increasing rigidity and lowering manufacturing costs. In this embodiment and others, this can include using solder joints between the sensor and the line or other joining techniques appropriate for the technology used for the communication line which are known in the art.

The remaining strings can have a similar configuration and, therefore, will not be discussed in detail herein in the interest of brevity. In addition, virtually any pattern of sensor arrangement could be used to obtain any desired internal schematic or matrix representation of the curing process for the concrete.

Sensor 70 can be formed by any method known in the art including, but not limited to, by including a sensor body 100 that is supported by clip 90 on wire 80 and this body can be an electronics board. Sensor 70 further includes an electrical structure 102 that provides the internal communication within sensor 70 between any devices that can be present in sensor 70. As can be appreciated, this can include any sensing device known in the industry including future sensing equipment that becomes known in the art. In this respect, sensor 70 can include a temperature measuring device 110 and can include one or more devices 111 for measuring pressure, sound, acceleration, vibration, resistivity, strain, capacitance, moisture, and/or chemicals. Sensor 70 can further include a memory store 112 that can store data, commands, position, and/or calibration data. Sensor 70 can further include a transmitting device 114 that can be a transmitter, receiver and/or a transceiver (wired—shown or wireless) which can be used to communicate data obtained by sensor 70 which will be discussed in greater detail below. Sensor 70 can further include an electronic identification code 120 corresponding to the set position of the sensor along the string axis so that information communicated by sensor 70 can be positioned within the cavity which allows for the creation of a detailed schematic representation of the data points within the cavity. As can be appreciated, FIG. 4 is only intended to be a schematic representation of the sensor which can be made in a wide range of forms and wherein components could be combined such as code 120 being part of memory store 112. Further, identification code 120 can be a unique address for each of the sensors.

Sensor 70 can further include a sensor housing 122 that partially or completely encapsulate sensor 70 and protect some or all electronics from the poured material in the pile cavity. This housing can be any housing known in the art including, but not limited to, a potting material, conformal coating and/or an applied polymeric coating. Further, as discussed above, this can include molding the sensor into the line. In another embodiment, the housing can be a clam shell housing configured to partially or fully encapsulate the electronics. Further, the housing can be a brushed on, spayed on or dipped on. Yet even further, this housing can be a partial housing wherein only the connection with the line is coated.

Sensors 70 can be then configured to monitor a set parameter such as temperature and temperature changes to allow the curing process to be accurately monitored and to ensure the proper curing of the poured material. The sensors can also be used to detect abnormalities within the poured structure based on differences in the readings of the sensors. This can be done by watching real time temperatures of each sensor and/or by compiling this information which will also be discussed in greater detail below.

As discussed above, the identification code or unique address of each sensor can be transmitted by way of electrical conductor 80 to allow for the determination of the exact position of the particular sensor so that its temperature reading can be oriented to a specific location within the pile cavity and a three dimensional schematic or matrix can be created. By including a sensor identification code, the information from the many sensors within the pile cavity can be located and itemized to obtain a clear three dimensional schematic picture of the temperature variations within the poured pile during the curing of the poured material. This information can be provided to a local engineer or even to an engineer at remote locations such that the detailed three dimensional schematics of multiple pouring can all be monitored at once at a single remote location. As can be appreciated, this information can also be fed into a computing device which can provide a three dimensional schematic diagrams of the curing process on a real time basis and all changes in temperature during the curing of the pile can be graphed and/or fed into computing system that can calculate or grade the integrity of the poured pile. As is known in the art, temperature abnormalities can be a sign of defects within the poured pile which can be factored into these calculations.

By utilizing inexpensive sensors attached to a hanging wire, a large number of sensors can be positioned in an array within the pile cavity. This array of sensors can provide detailed information not before possible with prior art devices. Further, since the sensors are fixed at a given location, human error is minimized. Yet even further, since the temperature sensors of sensor 70 are in direct contact with the concrete, greater accuracy is achieved. Further, triangulation techniques can be used to help create three dimensional schematic images of the curing data which again can be fed into a computing device to produce valuable information for determining the integrity of the entire poured pile.

In that each sensor has an identification associated with it and each sensor is positioned at a set position on the sensing string, if the string is positioned accurately within the pile cavity, an accurate representation of temperature changes and/or current temperatures of the entire pile can be calculated. Further, by including the wire string arrangement of the device of this application, additional temperature sensors can be positioned within the pile wherein the overall result is a more accurate three dimensional matrix of the temperature of the pile during the curing process. This is true in that each temperature string is much less expensive than the prior art temperature sensing devices and that these temperature sensing strings do not include an opened cavity as is necessary for prior art devices. This is in part obtainable in view of the low cost configuration of this sensing apparatus wherein it can be a disposable apparatus. However, as can be appreciated, in certain applications the temperature strings could be reused and/or reusable.

In yet other embodiments, strings 20, 22 can be joined to the rebar structure 50 by one or more clips 130 to better fix the set position of each sensor within the cavity and to reduce any movement of the string within the cavity during pouring. This again can be used to increase the accuracy of the temperature matrix or schematic that can be produced by the system.

Once the temperature strings are positioned within the pile cavity, they can be joined to an operating system or computing device 150 wherein temperature readings can be taken at any time and these temperature readings can be controlled electronically without human intervention. In this respect, once the system is set up for monitoring the pouring of the pile, the computer system can communicate with sensors 70 by way of transceiver 114 to read the temperature data at any time or at set intervals which can be used to create a three dimensional array or schematic of the pouring and/or curing temperatures of the pile in a real time manner, continuously and/or during set intervals. Then, once the pile is substantially cured, which takes approximately 18-30 hours, this data can be retrieved from a data store in device 150 or from data store 112 to evaluate the poured structure. This information can be reviewed locally or transmitted by a transceiver arrangement 152 to remote locations and reviewed. Further, real time review can be achieved either onsite or at a remote location if the data is transmitted from the site to the offsite location. This can include the use of transceivers within the sensing device and/or the onsite computer and computer data stored. Sensors 70 can communicate with device 150 wirelessly or by one or more sets of communication lines 160 and 162 that can be supported above the pile hole by a support 164.

With reference to FIGS. 2 and 3A-3D, the invention of this application can include string arrays of many forms. In this respect, any number of sensor strings can be utilized within system 10 to monitor a poured cavity according to aspects of this invention. FIGS. 3A-3D are examples of several such arrangements, but are not intended to show all possible arrangements. As can be appreciated, the increase in the number of sensor strings 21 utilized within system 10 can provide a more accurate schematic matrix of the characteristic that is to be monitored by system 10. All of these strings can be joined to a similar operating system 150 or can be connected to separate operating systems as is desired. Further, each string and/or sensor could have an operating system without detracting from the invention of this application. In addition, one or more sensor strings can have different spacings between the sensors without detracting from the invention of this application.

Figure 2:
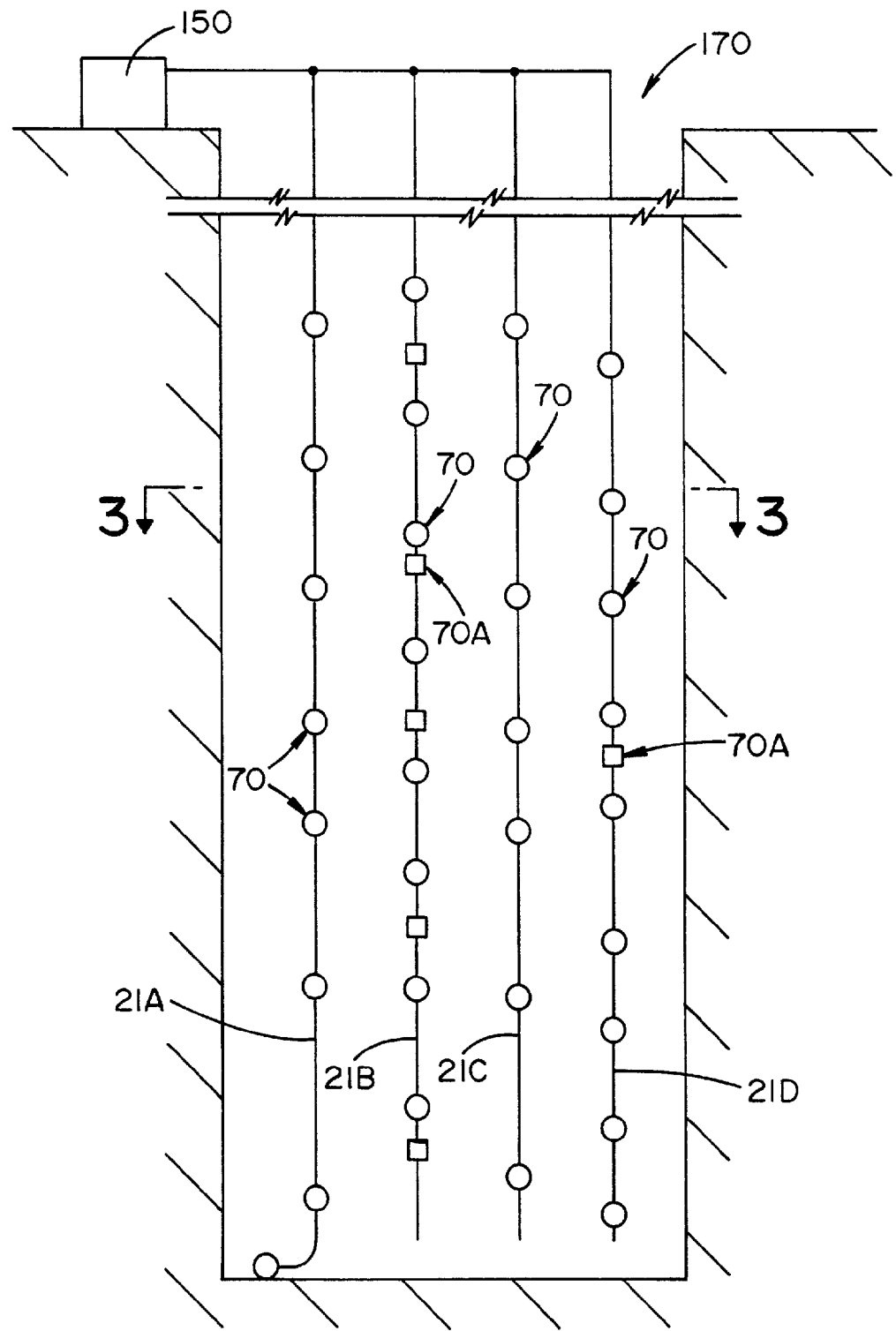
FIG. 2 is a sectional view of a drilled pile showing yet another embodiment of the invention of this application.
Figure 3A:
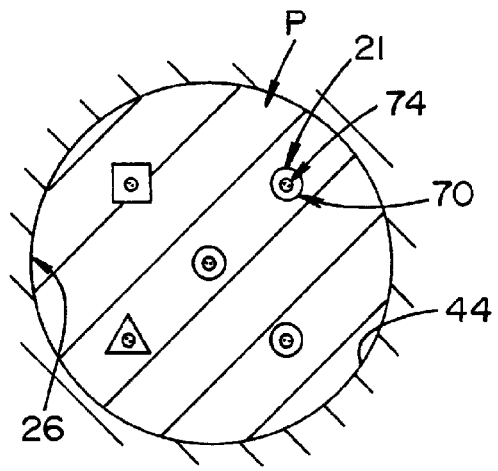
FIG. 3A is a sectional view taken along line 3-3 in FIG. 2 and shows other embodiment of the invention of this application.
Figure 3B:
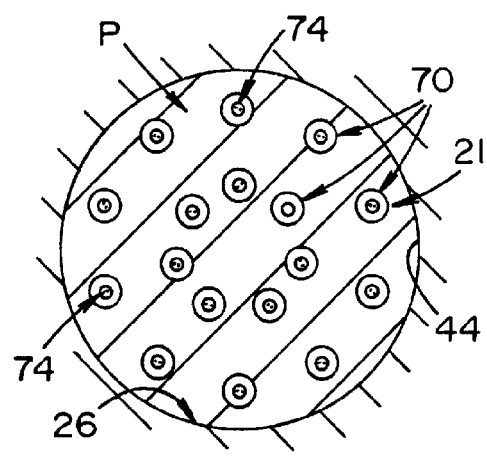
FIG. 3B is another sectional view taken along line 3-3 in FIG. 2 and shows a further embodiment of the invention of this application.
Figure 3C:
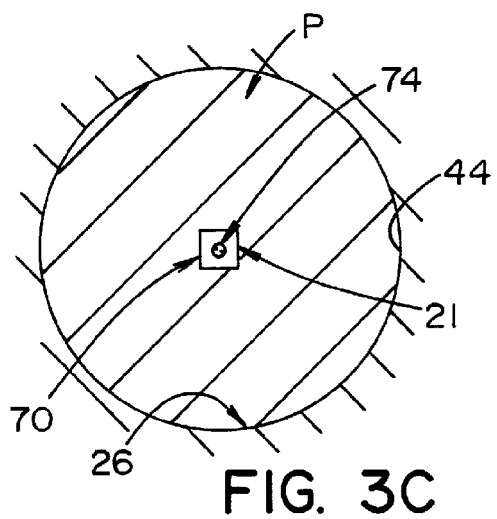
FIG. 3C is a further sectional view taken along line 3-3 in FIG. 2 and shows yet a further embodiment of the invention of this application.
Figure 3D:
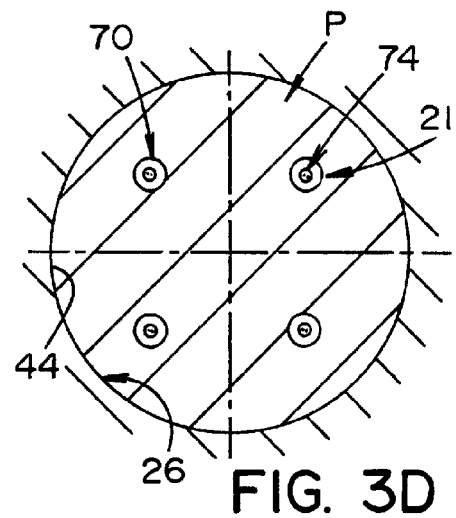
FIG. 3D is yet another sectional view taken along line 3-3 in FIG. 2 and shows yet another embodiment of the invention of this application.

In yet other embodiments, one or more sensor strings can have more than one sensor arrangement such that, for example only, every other sensor includes a temperature sensor while the other sensors within the string include a one of the other sensors referenced above. While this may reduce the resolution of the matrix, separate parameters can be monitored separately. Shown in FIG. 2 is a sensor arrangement 170 having sensor strings 21A-21D. Sensor string 21A includes only sensor 70 having temperature sensors only while string 21B includes both sensors 70 and sensor 70A wherein sensor 70A have on or more of these other sensors. String 21C shows sensors at different spacings which, again, can be used to adjust the matrix produced by the system. String 21D includes both sensors 70 and sensor 70A wherein sensor 70A is at a different location within the cavity.

Figure 5:
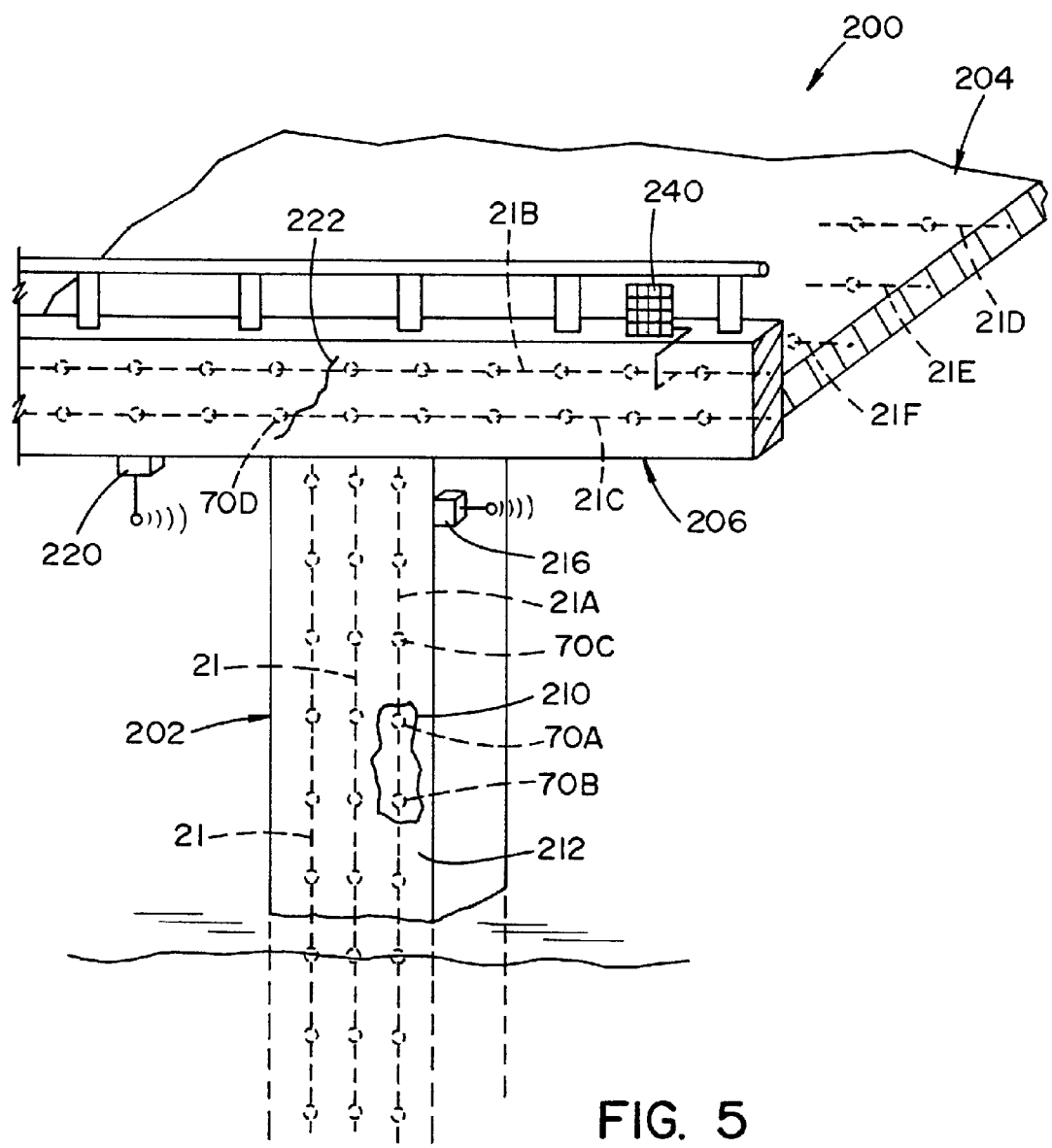
FIG. 5 is a perspective view of a portion of a superstructure showing certain applications of the devices of this application.
Figure 6:
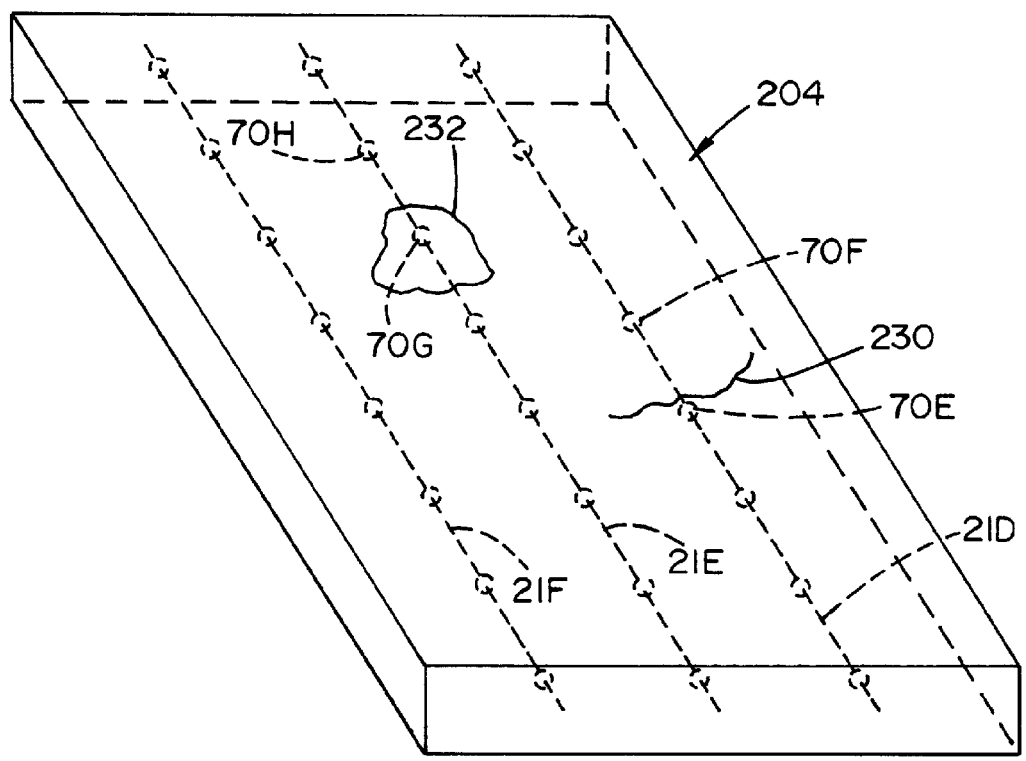
FIG. 6 is a perspective view of the roadway deck taken from FIG. 5.

With reference to FIGS. 5 and 6, shown are examples of yet other uses of the invention of this application. In this respect, shown is the use of the device of this application to monitor some or all portions of structures and/or superstructures even after the construction phase. In this respect, as is discussed in greater detail above, the strings of this application can form a permanent part of the poured structure in that the cured material is poured directly onto the string array of the sensors of this application wherein they are permanently cast into the pile or support structure. This not only provides a cost savings and an accuracy improvement as is discussed above, but it can also be utilized to monitor the structure even after the construction is completed. In this respect, the sensing devices and the operating system can be operated after the completion to continually monitor physical characteristics such as temperature changes to allow for defect determination during the operation of the structure or for any other reason.

Shown is a perspective view of a roadway structure having one or more sensing systems according to certain aspects of this application embedded into multiple components of this superstructure. More particularly, bridge structure 200 includes a pile 202, a road deck 204, and a side abutment 206. Each of these components can include one or more sensor strings 21 which can be both utilized during the pouring process of these structures and even after the completion of the roadway.

Temperature changes can be a sign of an abnormality within these structures during the pouring process and after the structure is fully cured. With respect to pile 202, an abnormality 210 is shown on a side portion 212 of the pile. Sensor string 21A runs through this abnormality and can be used to help detect the abnormality so the work crew can evaluate and fix the abnormality before the damage is too severe. In this respect, sensor 70A and 70B are within abnormality 210 and sensor 70C is adjacent thereto. In that sensors 70A and 70B are more exposed to the environmental elements, they can register a greater temperature changes than sensor 70C. This information can be stored short term or long term and/or can be transferred by way of a removable memory store, an information output (such as by way of a USB port or wirelessly. Or, this information can be communicated by way of a transceiver 216 to a remote monitoring station which can then use this information to determine whether or not there is a chance of an abnormality or defect within this structure. Then, once it is determined that there is a defect or abnormality within the pile structure is likely, a service crew can be sent to review the structure and to confirm whether or not work needs to be done. This can be used to more efficiently dispatch work crews to possible structural problems. In yet other embodiments, the system and/or a monitoring station can produce a signal that can be detected by a passing road working vehicle to signal the road crew to stop and check for a possible abnormality.

Similarly, side structure 206 can include sensor strings 21B and 21C joined to a transceiver 220 wherein a defect shown as a crack 222 can produce a temperature deviation in sensor 70D as opposed to adjacent sensors within this structure. Again, the data can be monitored over a period of time to determine whether or not further action is needed to fix this structure.

The same is true for roadway 204 which, in this drawing, includes a crack 230 and a pothole 232 which passes near certain sensors. Crack 230 passes near sensor 70E of string 21D wherein sensor 70E can detect temperature changes greater than an adjacent sensor 70F such that a monitoring station and/or system can determine with a reasonable amount of certainty that further action is needed and a work crew needs to be sent out to the particular location. By including these monitoring arrangements, work crews can be dispatched more efficiently based on real time information produced from the system.

Similarly, road surface conditions can also be monitored. For example, the sensors can be used to help detect a pothole 232 which is near sensor 70G. Again, temperatures changes of sensor 70G can be compared to temperature changes of adjacent sensor 70H to help determine that there is a possible defect in the road surface. In yet other embodiments, this could be use to detect road condition such as icing conditions in the winter.

In yet other embodiments, the system could use an energy harvester 240 which can be any energy harvester now known in the art or known in the future art which includes, but is not limited to, a solar power system and a device that produces power by use of vibration. The energy harvester can be used to produce the necessary power needed to operate the system. This can be helpful for remote applications that do not have an power source. Further, the system to could operate wherein information is only transmitted at set intervals to further conserve energy usage.

Figure 7:
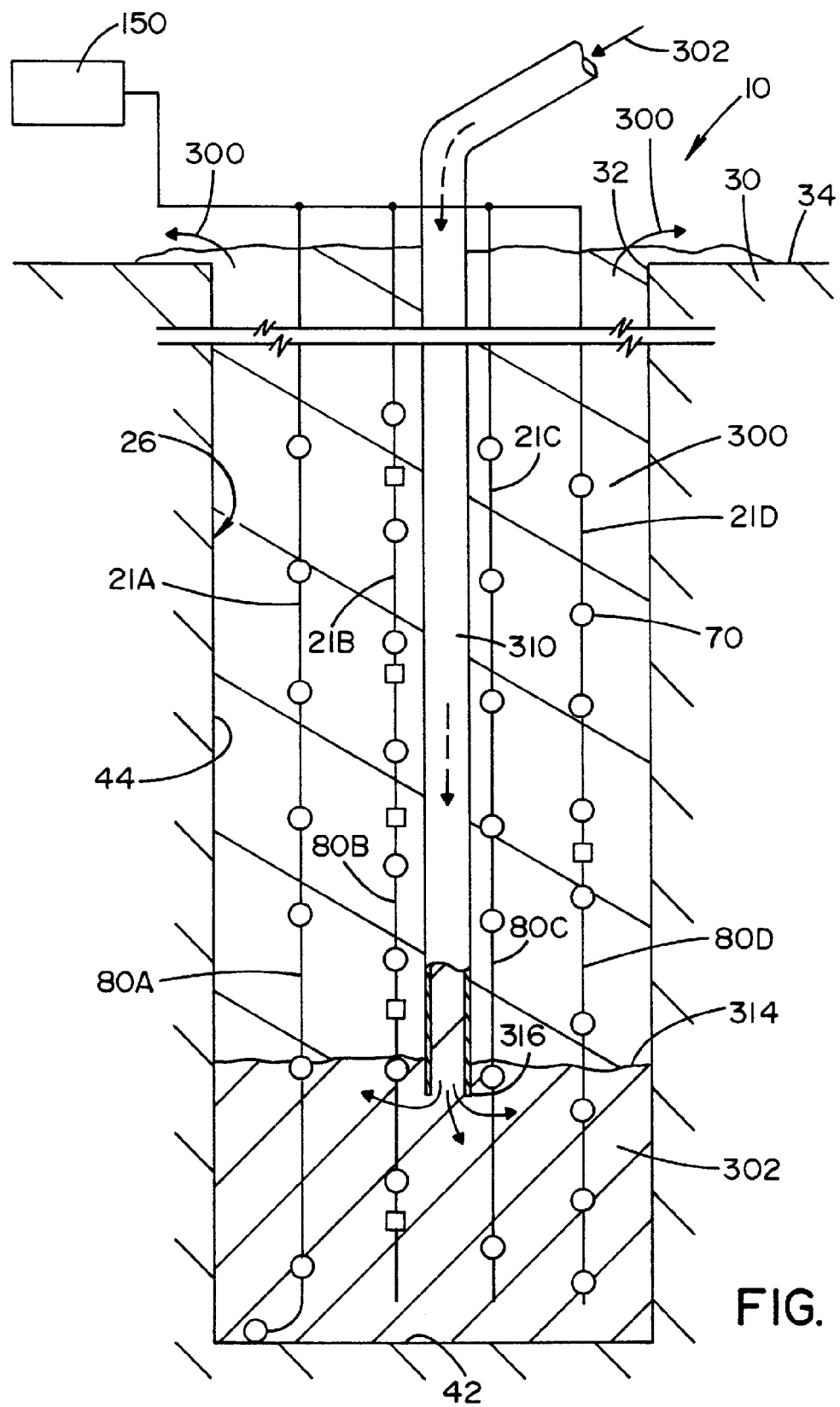
FIG. 7 is a sectional view of a pouring operation according to yet another aspect of the present invention.

With reference to FIG. 7 shown is the pouring of a cast pile which represents one set of embodiments of the invention of this application. More particularly, shown is sensing system 10 of this application utilized during the pouring or filling of the pile cavity. In this respect, the filling of a pile cavity can be a difficult procedure in that a slurry 300 is often pumped into pile cavity 26 to maintain the integrity of cavity walls 44 before and during the pouring of the concrete into the cavity.

More particularly, shown is a pouring process wherein a concrete 302 is being pumped into cavity 26 by way of a fill tube 310 that is positioned in the cavity such that concrete 302 is pumped or poured through tube 310 starting near bottom 42 of the cavity. This process forces slurry 300 upwardly and out of top 32 of cavity 26. As a result, slurry 300 is forced upwardly within the cavity as the concrete is pumped into the bottom portion of the cavity. As a top extent or level 314 of concrete 302 rises in the cavity, fill tube 310 must be pulled upwardly from the bottom of the cavity such that a bottom 316 of fill tube 310 remains in close proximity to extent 314 between concrete 302 and slurry 300. However, removing the fill tube too quickly such that end 316 moves above extent 314 into the slurry 300 can create imperfections in the poured pile. On the other hand, keeping the fill tube too deep within the concrete portion below extent 314 prevents the concrete from flowing out of the tube and puts undue strain on the concrete pumping equipment.

As a result, there is a need to monitor this process and maintain the opening of the fill tube as close as possible to extent 314 but below extent 314. Prior art filling techniques include monitoring the volume of concrete being pumped into the pile cavity and using this information to determine the rate in which the fill tube is to be withdrawn from the hole. In that removing the fill tube too quickly can produce pile imperfections, error is always on the side of keeping the fill tube too deep within the hole which adversely affects the efficiency of the process and reduces the expected service life of the equipment.

By utilizing the sensing system according to the invention of this application, the dividing line between the concrete and the slurry can be accurately detected by changes in temperature at each sensor 70. This accuracy can be achieved in that these sensors are all at a known location within the pile cavity. As line passes by a sensor, it will begin to show a temperature increase produced by the curing of the concrete. This information can be communicated to the operators of the filling operations wherein this filling line can be accurately monitored and can be the basis of the rate of withdrawal of fill tube 310 from cavity 26.

In one embodiment, the sensors are strung every six inches on the sensing strings and the sensing device can be activated during the pouring process. The data produced by these sensors can be communicated by way of communication lines 80A-80D of strings 21A-21D to an operating system or display wherein the operators in charge of the filling operation can have real time information on the changing level of extent 314 within the cavity. This information can then be used to withdraw the fill tube and to maintain the opening of the fill tube at a desired location beneath the slurry/concrete dividing line. In another embodiment, this information can be sent directly to an operating system of the filling operation such that the filling tube is automatically controlled based on the information received from the sensors.

Then, once the pouring process is completed, the sensing strings can remain in place and can be used to monitor the curing process as is described above. As a result, the sensors according to the invention of this application both help in the pouring process and, then, help determine the integrity of the pile after the process is complete. Yet even further, the sensors can be utilized for other sensing applications after the pile has been cured in that the sensors remain within the pile. This information can be utilized to ensure that the proper pouring has been achieved and that the proper mix of concrete was poured.

In one embodiment, the system can be used to determine when the pile has cured to a desired state to help accelerate the construction process. In that loading a pile prematurely can damage the structural integrity of the pile, work crews typically wait a full 28 days before any load is applied to the pile. This 28 day period is based on industry data that poured materials, such as concrete and grout, will be cured in 28 days. However, in that it was previously difficult to determine the point in which a pile has actually reached a "fully cured" condition, a significant safety factor is present in this 28 day cure cycle and the pile actually may reach a "full cure" well before the 28 days. Thus, time can be lost to ensure that the pile is properly cured. The system of this application can be used to determine when the pile has reached an "initial cure" which normally takes approximately 18-30 hours. Then, the system can remain active to determine when the pile or structural member is "fully cured" so that the construction crew is not forced to wait the entire 28 days. In many situations, the poured material can be "fully cured" well before the 28 days and this information can be used to shorten the delay between pouring the pile and applying a load to the pile. With road applications, this information can shorten the delay between pouring a road surface and allowing vehicles to drive on this road surface. As can be appreciated, this information can be used in any application to determine the point of reaching a "full cure" so that the curing lead time is reduced. As can also be appreciated, the opposite can be true wherein there are situations where a structural member is not "fully cured" in 28 days wherein the system of this application can be used to warn the workers and help prevent the premature loading of the structure. This cure testing can include testing the level of hydration energy of the pile to determine the state of the curing process. The absence of hydration energy could be used to determine the point of "full cure." Again, once the pile reaches the desired hydration energy or "full cure," the pile can be loaded or the structure can be used.

In yet other embodiments of the invention of this application, the temperature strings could be positioned within longitudinally extending passages such as those formed by PVC pipe positioned within the pile cavity before the pouring of the pile. While in these tubes, the location of the sensor is still fixed and can produce the temperature matrix described in other embodiments of this application, but which allows the strings to be removed and reused.

In further embodiments, the communication line can include multiple transmission points. In this respect, in one group of embodiments, the transmission line has a first and a second end wherein one of these ends is a transmission end that can be joined to an operating system or even to a transmitting device to communicate the data from the sensor for processing and/or analyzing. In other embodiments, both the first and the second end can be transmission ends for this communication of data. Yet further, the line can have one or more additional transmission points 350 (see FIG. 1) even between the first and second ends of the lines and these strings can also have more than two ends. In one embodiment, the line includes transmission point 350 between the first and second ends wherein this transmission point is joined to the operating system by any method known in the art including a direct line connection or even a radio frequency "RF" connection. In another embodiment, this transmission point is a line connector 352 joining two adjacent lines or all lines in the system. As can be appreciated, a failure in any of the communication lines could result in loss of all data for an entire string of sensors. By including multiple transmission points, the loss can be reduced to only a portion of the string. In yet other embodiments, each sensor can be a transmission point wherein each sensor would include a transceiver configured to be directly connected to an operating system by any means known in the art including, but not limited to, RF communication.

In yet other embodiments, the wire strings of this application can be mass produced in any one of a number of configurations. In one such configuration would be wires produced having 100 sensors located at specific distances wherein each sensor from 1 to 100 can have a built in electronic location identification so that each temperature reading is associated with a specific sensor and a specific location on the wire. In other embodiments, the identification code or address can be assigned after the production of the string or even on site as is needed. Further, the sensing wires according to other aspects of this application could be produced in a plurality of standard lengths having a number of sensors according to the particular length. For example, five different lengths of sensing wire strings could be produced wherein each of the five sizes would be, for example, 15, 25, 35, 65 and 100 meters long and the end user would choose from one or more of these sizes (or others) based on the dimensions of the pile to be poured. In yet other embodiments, these set length strings could include connecting devices at both ends such that more than one standard string could be connected in series. Caps could be used to cover the base of the last string in any given series. In other embodiments, the strings can be produced in custom lengths based on the application or use or the product or based on customer requests. In yet other embodiments, the strings can be cut or customized on site and the cut portion sealed or properly terminated such as by a termination resistor. These wire strings could be in spool form and can include markings to designate the identification of each of the sensors within the wire. For example, these identifications could be numbered from 1 to 100 with the first sensor being the top sensor and the highest number sensor being the lowest sensor within the pile cavity. This information can be noted during the positioning of the wire string within the wire cavity wherein each of the sensors can be positioned at a known location within the pile cavity such that the three dimensional array can be created once the information is transmitted from the sensors to the monitor and/or computing device.

As discussed above, the system of this application can use other sensing devices beyond temperature sensors without detracting from the invention of this application. These other devices could be part of sensor 70 or these other devices could be separate from sensor 70 along line 74. Further, these other sensor devices could be mounted at the factory or on site and could be used in any pattern such as in an alternating pattern with sensors 70 such that each sensor can produce its own three dimensional array. Further, in yet other embodiments of this application, the temperature sensors and these other sensing devices can be utilized in connection with other testing procedures. In this respect, as is discussed above, the system of this application can include one or more other sensing devices such as devices for measuring pressure, sound, acceleration, vibration, resistivity, strain, capacitance, moisture, and/or chemicals. These other devices can be utilized for procedures such as sound testing wherein the top of the pile is tapped with a hammer and the resulting sound waves are analyzed. The system of this application can include sensors to detect and/or record these sound waves to help test for imperfections in the pile.

The invention of this application could also be used for energy pile systems wherein flow paths in a poured pile are used to heat and/or cool a building structure similar to that of geothermal heating and cooling systems. The invention of this application can be used to measure the energy of or in the pile and to determine if the pile has reached its limits in geothermal energy transfer. This information can be utilized to help the heating and cooling system run more efficiently and to determine points were secondary cooling and/or heating methods are needed supplement the energy harvested from the pile.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

It is claimed:

1. A system for generating a thermal matrix to analyze the integrity of a poured structure that is formed by introducing a curable material into a cavity and the curable material solidifying in the cavity to form a formed structure, the system comprising at least one sensor string having a support line defining a string axis and a group of independent thermal sensors joined to the support line and spaced along the support line, each sensor of the group being joined to the support line at a fixed location forming gaps having known spacings therebetween, each thermal sensor being configured to measure temperature in a fixed sensor range extending around the thermal sensor and to operate independently of and generally simultaneously with other thermal sensors in the sensor group, each thermal sensor of the group of thermal sensors having a unique electronic identification code corresponding with the particular sensor and the known and fixed position of the particular sensor along the string axis, each thermal sensor being configured to produce temperature data of an associated curable material in the fixed sensor range independent of the temperature detection of other thermal sensors in the group of sensors and at the same time as the other thermal sensors in the group of sensors, the system further including a computing device configured to receive the individual temperature data and the unique electronic identification codes from thermal sensors in the group of thermal sensors and combine the independent data to calculate a thermal string matrix of thermal activity associated with the associated curable material from temperature data taken from multiple thermal sensors in the sensor group and temperature data generated by the multiple thermal sensors at generally the same time.

2. The system of claim 1, wherein the associated cavity is a ground opening in a ground layer extending from a ground surface to a bottom extent below the ground surface.

3. The system of claim 1, wherein the fixed sensor range of one sensor in the group of sensors partially overlaps with the fixed sensor range of at least one adjacent sensor of the group.

4. The system of claim 1, wherein the detection of the test temperatures of the thermal string matrix is selective measurement of all the test temperature of the sensor group at designated time intervals for the analysis of the associated curable material.

5. The system of claim 1, wherein the sensor string includes a first sensor string forming a first group, the system further including a second sensor string forming a second group and a third sensor string forming a third group, the thermal string matrixes of the three groups forming a three dimensional thermal matrix associated with the curing cycle of the associated curable material from temperature readings taken from all three groups of sensors at generally the same time.

6. The system of claim 5, wherein the three dimensional thermal matrix is a real time matrix for a substantial portion of the curing cycle.

7. The system of claim 1, wherein the thermal matrix is a real time thermal matrix taken at designated intervals for a substantial portion of the curing cycle.

8. The system of claim 1, wherein the gaps between thermal sensors are less than 1 foot.

9. A sensor string for generating a thermal matrix that is positionable within a volume of material such as a volume of curable material to form a formed solid object, the sensor string comprising a support line extending along a string axis between a first end and a second end, the sensor string further including a plurality of independent thermal sensors joined to the support line between the first and second ends and fixed to the support line at known intervals such that the each thermal sensor is in a general known and set position along the support line and there are gaps between adjacent thermal sensors having known spacings, each thermal sensor of the plurality of independent thermal sensors being configured to measure temperature in a fixed sensor range extending around the thermal sensor and to operate independently of and generally simultaneously with other thermal sensors of the plurality of thermal sensors, each thermal sensor of the plurality of thermal sensors including a unique electronic identification code corresponding to the set position along the support line, each thermal sensor being configured to produce temperature data in an associated material encapsulating the thermal sensor in the fixed sensor range independent of the temperature detection of other thermal sensors of the plurality of thermal sensors and at generally the same time as other thermal sensors of the plurality of thermal sensors such that independent and combined data produced from the thermals sensors of the plurality of thermal sensors is configured to produce a thermal string matrix of thermal activity associated with the associated material.

10. The sensor string of claim 9, wherein the support line is a communication line having at least two wire conductors each having an outer jacket surrounding the wires.

11. The sensor string of claim 9, wherein the cavity has a first extent and a second extent and the sensor string is positionable in a generally fixed operating position within the cavity, the sensor string extending between the first and second extents and the plurality of sensors being encapsulated by the associated material below the a top extent of the associated material and remaining in the generally fixed operating position within the associated material at least until after the desired thermal matrix is generated.

12. The sensor string of claim 9, wherein the associated material is an associated-curable material and plurality of sensors being encapsulated by the associated material below the a top extent of the associated material and permanently remaining in the generally fixed operating position within the associated curable material after the curing cycle.

13. The sensor string of claim 9, wherein the known intervals are generally equal.

14. The sensor string of claim 9, wherein the each thermal sensor includes a memory store, the memory store including instructions for a transmitting device for the selective communicating and storing of data including the temperature data and the unique identification code.

15. A plurality of sensor strings for generating a three dimensional thermal matrix that are positionable within a volume of fluid material such as a volume of curable material to form a formed solid object, each sensor string of the plurality of sensor strings comprising a support line extending along a string axis between a first end and a second end, the sensor string further including a plurality of independent thermal sensors joined to the support line between the first and second ends and fixed to the support line at known intervals such that the each thermal sensor is in a general known and set position along the support line and there are gaps between adjacent thermal sensors having known spacings, each thermal sensor of the plurality of independent thermal sensors being configured to measure temperature in a fixed sensor range extending around the thermal sensor and to operate independently of and generally simultaneously with other thermal sensors of the plurality of thermal sensors, each thermal sensor of the plurality of thermal sensors including a unique electronic identification code corresponding to the set position along the support line, each thermal sensor being configured to produce temperature data in an associated material encapsulating the thermal sensor in the fixed sensor range independent of the temperature detection of other thermal sensors of the plurality of thermal sensors and at generally the same time as other thermal sensors of the plurality of thermal sensors such that independent and combined data produced from the thermals sensors of the plurality of thermal sensors is configured to produce a thermal string matrix of thermal activity associated with the associated, the combined data from each of the sensor string being combinable to produce a three dimensional thermal string matrix.

* * * * *